(12) United States Patent
Masuda et al.

(10) Patent No.: US 6,878,382 B2
(45) Date of Patent: Apr. 12, 2005

(54) PERSONAL CARE COMPOSITION COMPRISING HYDROPHOBIC GEL

(75) Inventors: Hisatoshi Masuda, Moriyam (JP); Mayu Ishigami, Ashiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 216 days.

(21) Appl. No.: 10/396,948

(22) Filed: Mar. 25, 2003

(65) Prior Publication Data

US 2003/0215477 A1 Nov. 20, 2003

Related U.S. Application Data

(63) Continuation of application No. PCT/US00/26492, filed on Sep. 26, 2000.

(51) Int. Cl.[7] ............................. A61K 7/00; A61K 7/025
(52) U.S. Cl. ........................................... 424/401; 424/64
(58) Field of Search ..................................... 424/401, 64

(56) References Cited

U.S. PATENT DOCUMENTS 5,747,049 A * 5/1998 Tominaga .................... 424/401
5,843,407 A 12/1998 El-Nokaly et al.
5,871,759 A 2/1999 Hamano et al.

FOREIGN PATENT DOCUMENTS

| EP | 0775496 A1 | 5/1997 |
| GB | 1 2223 220 | 2/1971 |
| WO | WO 95/11000 | 4/1995 |
| WO | WO 97/01356 | 1/1997 |
| WO | WO 00/47182 | 8/2000 |

* cited by examiner

*Primary Examiner*—James M. Spear
*Assistant Examiner*—Sharon Howard
(74) *Attorney, Agent, or Firm*—Vlad Vitenberg; Tara M. Rosnell

(57) ABSTRACT

Disclosed is a personal care composition comprising by weight:
(a) from about 5% to about 35% of a hydrophobic gel comprising:
 (i) a cholesteryl derivative;
 (ii) an oil swelling clay material;
 (iii) a non-volatile liquid oil; and
 (iv) a polar solvent; and
(b) a carrier which is substantially free of water, surfactant, and lecithin;
which satisfies the need for a personal care composition having improved physical stability.

6 Claims, No Drawings

PERSONAL CARE COMPOSITION COMPRISING HYDROPHOBIC GEL

CROSS REFERENCE TO RELATED APPLICATION

This is a continuation of International Application PCT/US00/26492, with an international filing date of Sep. 26, 2000

FIELD OF THE INVENTION

The present invention relates to personal care compositions comprising a hydrophobic gel. The composition is particularly useful for making lipsticks, foundations, and creams.

BACKGROUND

Lipsticks are primarily made of lipophilic or hydrophobic materials. Lipsticks designed for providing a moisturizing benefit to the lips further contain water, polar solvents, or other moisturizing components which are more or less hydrophilic. The use of association structures have been suggested to bind such moisturizing components in the lipophilic matrix of the lipstick. While such lipstick compositions provide a favorable moisturizing benefit to the lips, they were not completely satisfactory in terms of physical stability, color stability, and sweat resistance.

Physical stability relates to the stability of the stick during storage and upon use. For example, a stable stick does not deform during storage at ambient temperature, and does not bend or break upon normal condition use. Color stability relates to the stability of color during storage and after applied on the lip. It has been known that lipsticks containing a high amount of moisturizing components have the tendency to change color over time after applied on the lip. Sweating is a phenomena seen on the surface of sticks, and is believed to be due to oils and/or solvents separating and leaking out of the lipophilic matrix of the stick. Sweating provides a negative appearance to the user.

Emulsion compositions utilizing cholesteryl derivatives and swelling clay material are disclosed, for example, in Japanese publication A-8-20529. While such emulsion is believed to provide physical stability to the composition, further improvement is desired.

Based on the foregoing, there is a need for a lipstick composition which has improved physical stability, improved color stability, and improved sweat resistance, while also providing moisturizing benefit to the lips. There is also a need for a personal care composition which has improved physical stability over a wide range of viscosity and/or hardness.

SUMMARY

The present invention is directed to a personal care composition comprising by weight:
(a) from about 5% to about 35% of a hydrophobic gel comprising:
  (i) a cholesteryl derivative;
  (ii) an oil swelling clay material;
  (iii) a non-volatile liquid oil; and
  (iv) a polar solvent; and
(b) a carrier which is substantially free of water, surfactant, and lecithin;
  which satisfies the need for a personal care composition having improved physical stability.

The present invention is further directed to a lipstick composition which satisfies the need for improved physical stability, improved color stability, and improved sweat resistance, while also providing moisturizing benefit to the lips.

The present invention is still further directed to suitable methods of preparing the compositions above.

These and other features, aspects, and advantages of the present invention will become evident to those skilled in the art from a reading of the present disclosure with the appended claims.

DETAILED DESCRIPTION

The following is a list of definitions for terms used herein.

"Comprising" means that other steps and other ingredients which do not affect the end result can be added. This term encompasses the terms "consisting of" and "consisting essentially of".

All percentages are by weight of total composition unless specifically stated otherwise.

All cited references are incorporated herein by reference in their entireties. Citation of any reference is not an admission regarding any determination as to its availability as prior art to the claimed invention.

All ratios are weight ratios unless specifically stated otherwise.

The present invention, in its product and process aspects, is described in detail as follows.

Cholesteryl Derivative

The composition of the present invention comprises a cholesteryl derivative having high water holding ability. The cholesteryl derivative useful herein provides the hydrophobic gel together with the oil swelling clay material, non-volatile liquid oil, and polar solvent. Without being bound by theory, it is believed that the cholesteryl derivative holds the polar solvent, thereby provides a stable gel.

The amount of cholesteryl derivative included is adjusted depending on the amount of polar solvent. Namely, when a high amount of polar solvent is desired, a high amount of cholesteryl derivative is included to effectively hold the polar solvent. For providing lipstick compositions, the cholesteryl derivative is comprised by weight of the entire composition at from about 2% to about 7%, preferably from about 3% to about 6%.

Cholesteryl derivatives useful herein include cholesterol and a C12-22 fatty acid or hydroxy fatty acid having high water holding ability, preferably cholesteryl 12-hydroxystearate, cholesteryl macadamiate, Cholesteryl Stearate, and mixtures thereof. Commercially available cholesteryl derivatives include cholesteryl 12-hydroxystearate with tradename Salacos HS available from Nisshin Oil Mills, Ltd., and cholesteryl macadamiate with tradename YOFCO MAC available from Nippon Fine Chemical Co., Ltd.

Oil Swelling Clay Material

The composition of the present invention comprises an oil swelling clay material which was high oil swelling ability. The oil swelling clay material useful herein provides the hydrophobic gel together with the cholesteryl derivative, non-volatile liquid oil, and polar solvent. The oil swelling clay material is first swelled with the non-volatile liquid oil prior to mixing with other components for making the hydrophobic gel. Without being bound by theory, it is believed that the oil swelling clay material, while absorbing the non-volatile liquid oil, further holds the closely bonded cholesteryl derivative and polar solvent within its structure.

The oil swelling clay material functions as a thickener for the composition. Thus, the amount of oil swelling clay material included is adjusted depending on the desired viscosity and hardness of the composition. For providing lipstick compositions, the oil swelling clay material is comprised by weight of the entire composition at from about 0.1% to about 1%, preferably from about 0.2% to about 0.5%.

Oil swelling clay materials useful herein include hectorite, bentonite, montmorillonite, and bentone clays which have been modified to be compatible with oil. Preferably, the modification is quaternization with an ammonium compound. Preferable oil swelling clay materials include quaternary ammonium modified hectorite. Commercially available oil swelling clay materials include benzyldimethyl stearyl ammonium hectorite with tradename Bentone 38 CG OR available from Rheox. Inc.

Non-Volatile Oil

The composition of the present invention comprises a non-volatile oil suitable for personal use. For providing the hydrophobic gel for lipstick compositions, the non-volatile oil is comprised by weight of the entire composition at from about 2% to about 10%, preferably from about 4% to about 7%.

The non-volatile oil useful herein may also be used in the carrier depending on the characteristics desired for the product. In such a case, preferably, the non-volatile oil to be used for making the hydrophobic gel is independently mixed with the other components for making the hydrophobic gel. The non-volatile oil to be used for making the carrier would thus preferably be mixed with other components for making the carrier, if present; and the hydrophobic gel and carrier would be finally mixed together to make the composition of the present invention.

Non-volatile oils useful herein are, for example, tridecyl isononanoate, isostearyl isostearate, isocetyl isosteatrate, isopropyl isostearate, isodecyl isonoanoate, cetyl octanoate, isononyl isononanoate, diisopropyl myristate, isocetyl myristate, isotridecyl myristate, isopropyl myristate, isostearyl palmitate, isocetyl palmitate, isodecyl palmitate, isopropyl palmitate, octyl palmitate, caprylic/capric acid triglyceride, glyceryl tri-2-ethylhexanoate, diglyceryl sebacate, neopentyl glycol di(2-ethyl hexanoate), diisopropyl dimerate, tocopherol, tocopherol acetate, avocado oil, camellia oil, turtle oil, macadamia nut oil, corn oil, mink oil, olive oil, rapeseed oil, eggyolk oil, sesame oil, persic oil, wheat germ oil, pasanqua oil, castor oil, linseed oil, safflower oil, cotton seed oil, perillic oil, soybean oil, peanut oil, tea seed oil, kaya oil, rice bran oil, china paulownia oil, Japanese paulownia oil, jojoba oil, rice germ oil, glycerol trioctanate, glycerol triisopalmitate, trimethylolpropane triisostearate, isopropyl myristate, glycerol tri-2-ethylhexanoate, pentaerythritol tetra-2-ethylhexanoate, lanolin, liquid lanolin, liquid paraffin, squalane, vaseline, and mixtures thereof. Commercially available oils include, for example, tridecyl isononanoate with tradename Crodamol TN available from Croda, Hexalan available from Nisshin Oil Mills, Ltd., and tocopherol acetates available from Eisai.

Non-volatile oils useful herein also include polyalkyl or polyaryl siloxanes with the following structure (I)

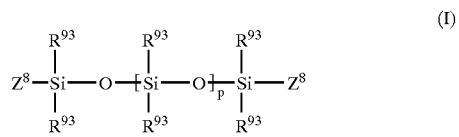

wherein $R^{93}$ is alkyl or aryl, and p is an integer from about 7 to about 8,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the skin, is compatible with the other components of the composition, and is chemically stable under normal use and storage conditions. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from the General Electric Company in their Viscasil® and SF 96 series, and from Dow Corning in their Dow Corning 200 series.

Polyalkylaryl siloxane fluids can also be used and include, for example, polymethylphenylsiloxanes. These siloxanes are available, for example, from the General Electric Company as SF 1075 methyl phenyl fluid or from Dow Corning as 556 Cosmetic Grade Fluid.

Non-volatile oils also useful herein are the various grades of mineral oils. Mineral oils are liquid mixtures of hydrocarbons that are obtained from petroleum. Specific examples of suitable hydrocarbons include paraffin oil, mineral oil, dodecane, isododecane, hexadecane, isohexadecane, eicosene, isoeicosene, tridecane, tetradecane, polybutene, polyisobutene, and mixtures thereof.

Polar Solvent

The composition of the present invention comprises a polar solvent which is soluble in water. The polar solvent provides the moisturizing benefit to the skin. The polar solvent also serves as solvent for incorporating water-soluble humectants which otherwise would not be compatible in the lipophilic carrier base. Without being bound by theory, it is believed that the polar solvent is held in the cholesteryl derivative and further trapped in the oil swelling clay material, to provide a stable hydrophobic gel.

For providing lipstick compositions, the polar solvent is comprised by weight of the entire composition at from about 0.01% to about 10%, preferably from about 1% to about 8%.

Polar solvents useful herein include polyhydric alcohols such as glycerin, 1,3-butylene glycol, propylene glycol, hexylene glycol, propane diol, ethylene glycol, diethylene glycol, dipropylene glycol, diglycerin, sorbitol, and other sugars which are in liquid form at ambient temperature. Also useful herein are water soluble alkoxylated nonionic polymers such as polyethylene glycol.

Commercially available polar solvents herein include: glycerin available from Asahi Denka; propylene glycol with tradename LEXOL PG-865/855 available from Inolex, 1,2-PROPYLENE GLYCOL USP available from BASF; 1,3- butylene glycol available from Daisel Kagaku Kogyo; dipropylene glycol with the same tradename available from BASF; diglycerin with tradename DIGLYCEROL available from Solvay GmbH; sodium hyaluronate with tradenames ACTIMOIST available from Active Organics, AVIAN SODIUM HYALURONATE series available from Intergen, HYALURONIC ACID Na available from Ichimaru Pharcos.

Water-Soluble Humectant

The composition of the present invention may further comprise a water-soluble humectant in an amount soluble in the polar solvent above, preferably from about 0.1% to about 10%, more preferably from about 1% to about 5%.

Water-soluble humectants useful herein in include niacinamide, panthenol, bacterial cultured mediums, allantoin, sodium lactate, PCA soda, amino acids, urea, sodium hyaluronate, chondroitin sulfate, collagen, elastin, pectin, carageenan, sodium alginate, trehalose, tuberose saccharide, chitin derivatives, chitosan derivatives, and mixtures thereof. Niacinamide and panthenol are commercially available, for example, by Roche.

Hydrophobic Gel

The hydrophobic gel can hold the polar and water-soluble material incorporated in the hydrophobic gel in a stable manner when contained in a lipophilic carrier. By changing the level and type of carrier, compositions containing the hydrophobic gel and having various viscosity and hardness can be made, ranging from firm sticks to thin creams. Personal care compositions containing the hydrophobic gel provide improved physical stability, such as in phase condition and viscosity. Without being bound by theory, it is believed that the hydrophobic gel herein possesses excellent thermal stability, thereby being stable under environments beyond ambient temperature.

The hydrophobic gel herein is preferably made by a method comprising the steps of:
(a) mixing the mixture of the cholesteryl derivative, the oil swelling clay material, and the non-volatile liquid oil at a speed of from about 1500 rpm to about 3000 rpm, preferably from about 1500 rpm to about 2500 rpm and at a temperature of from about 80° C. to about 95° C., preferably from about 88° C. to about 92° C.; and
(b) mixing the polar solvent with the mixture obtained in step (a) at a speed of at least about 4000 rpm, preferably from about 4000 rpm to about 8000 rpm, more preferably from about 5000 rpm to about 7000 rpm, and at a temperature of from about 85° C. to about 95° C., preferably from about 88° C. to about 92° C.

The mixing can be provided by any high shear mixer known in the art, such as those known as Homomixer or Disper. The hydrophobic gel herein is preferably made by mixing at a rotation speed higher than typically used for making personal care compositions, and in 2 steps. Without being bound by theory, it is believed that, in step (a), the mixture of components are mixed at a controlled rotation speed so that the oil swelling clay material is expanded to provide sufficient room for the cholesteryl hydroxystearate and subsequently added polar solvent to be entrapped within the oil swelling clay material, yet not too vigorous to destroy the structure of the oil swelling clay material. Without being bound by theory, it is further believed that, in step (b), the mixture of components are mixed at a high rotation speed so that the polar solvent is effectively entrapped in the oil swelling clay material. This is believed to provide the stability of the hydrophobic gel.

The hydrophobic gel thus obtained is then mixed with the carrier using conventional mixing means.

Carrier

The composition of the present invention comprises a carrier suitable for the desired use which is substantially free of water, surfactant, and lecithin. By being substantially free of such components, it is believed that the hydrophobic gel provides the physical stability, color stability, and sweat resistance to the composition. Further, by being substantially free of surfactants, a composition mild to the skin can be obtained. By "substantially free" what is meant is that none of water, surfactant, or lecithin is actively included in the composition. However, the present invention does not exclude the use of components which may carry an insignificant amount of water, surfactant, or lecithin as an impurity or byproduct. For example, it is known in the art that the polar solvents mentioned above may carry a small percentage of water. Such small amount of water is acceptable in the present composition. Typically, any of water, surfactant or lecithin, respectively, should be included at a level of less than about 1%, preferably less than about 0.5% of the entire composition.

As there is substantially no water, surfactant, or lecithin included, the carrier of the present composition is lipophilic in nature. Any component that is compatible with the hydrophobic gel can be used as a carrier. The carrier is selected to make various personal care compositions, including lipsticks, foundations, pigmented and non-pigmented creams for the skin or hair, antiperspirant sticks, and hair sticks. Solid waxes, gelling agents, non-volatile oils as mentioned above, powders, coloring pigments, and other lipophilic active components can be incorporated in the carrier. The non-volatile oils as mentioned above can be included in the carrier. The non-volatile oils used for the carrier can be the same or different from the non-volatile oils used for making the hydrophobic gel.

For making lipsticks, foundations, and creams, the carrier is selected from one or more of a solid wax, a non-volatile oil, a powder, and a coloring pigment. The composition is particularly suitable for making lipstick compositions which contain a solid wax and a coloring pigment in the carrier.

Solid Wax

The composition of the present invention may contain a solid wax. For providing lipstick compositions, the solid wax is comprised by weight of the entire composition at from about 10% to about 20%, preferably 12% to about 15%. The amount of the solid wax is controlled to provide the desired hardness and strength to the product.

The solid waxes useful herein are paraffin wax, microcrystalline wax, ozokerite was, ceresin wax, carnauba wax, candelilla wax, eicosanyl behenate, and mixtures thereof. A mixture of waxes is preferably used.

Commercially available solid waxes useful herein include: Candelilla wax NC-1630 available from Noda wax, Ozokerite wax SP-1021 available from Strahl & Pitsh, and Eicosanyl behenate available from Cas Chemical.

Powders and Coloring Pigments

The composition of the present invention may contain powders and color pigments. For providing lipstick compositions, the powders and color pigments component is comprised by weight of the entire composition at from about 1% to about 30%, preferably 2% to about 20%. The amount and type of powders and color pigments are selected depending on the desired characteristic of the product, for example, shade, coverage, UV protection benefit, and various skin feel.

The materials useful herein are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titate, ultramarine blue, Prussian blue, chromium oxide, chromium hydroxide, cobalt oxide, cobalt titanate, titanium oxide coated mica; organic powders such as polyester, polyethylene, polystyrene, methyl metharylate resin, cellulose, 12-nylon, 6-nylon, styrene-acrylic acid copolymers, poly proprylene, vinyl chloride polymer, tetrafluoroethylene polymer, boron nitride, fish scale guanine, laked tar color dyes, and laked natural color dyes.

A certain percentage of spherical pigments can be used. In a preferred embodiment, the materials are selected depending on the oil absorbing capability of the pigments. In one preferred embodiment, pigments having high oil absorbing capability and those having low oil absorbing capability are combined.

Hydrophobically treated pigments can also be used. Such hydrophobically treated pigments are made by treating the base material, as above, with a hydrophobical treatment agent, including: silicone such as Methicone, Dimethicone and perfluoroalkylsilane; fatty material such as stearic acid; metal soap such as aluminium dimyristate; aluminium hydrogenated tallow glutamate, hydrogenated lecithin, lauroyl lysine, aluminium salt of perfluoroalkyl phosphate, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such additional components generally are used individually at levels of no more than about 5% by weight of the composition. The composition of the present invention may further contain a nonvolatile dispersed silicone usually referred to as silicone gum. The term "silicone gum", as used herein, means a polyorganosiloxane material having a viscosity at 25° C. of greater than or equal to 1,000,000 mPa·s. Silicone gums are believed to provide wearability improvement such as long-lasting effect. The "silicone gums" will typically have a mass molecular weight in excess of about 200,000, generally between about 200,000 and about 1,000,000. Specific examples include polydimethylsiloxane, poly (dimethylsiloxane methylvinylsiloxane) copolymer, poly (dimethylsiloxane diphenylsiloxane methylvinylsiloxane) copolymer and mixtures thereof. Commercially available silicone gums are described in General Electric Silicone Rubber Product Data Sheets as SE 30, SE 33, SE 54 and SE 76.

The composition of the present invention may further contain a silicone resin, which are highly crosslinked polymeric siloxane systems. Silicone resins are believed to enhance spreadability and improve the feel to the skin. The crosslinking is introduced through the incorporation of trifunctional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units, and hence, a sufficient level of crosslinking, such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinylchlorosilanes, and tetrachlorosilane, with the methyl substituted silanes being most commonly utilized. Preferred are crosslinked silicone powders with tradenames Trefil E-505C, Trefil E-506C, and 9506 Powder; suspensions of silicone elastomer powders with tradenames BY29-119 and BY29-122; and silicone compound emulsions with tradenames SH5500, SC5570, and SM 5571; all available from Dow Corning.

Other useful silicone resins are silicone resin powders such as the material given the CTFA designation polymethylsilsequioxane, which is commercially available as Tospearl™ from Toshiba Silicones.

Silicone materials and silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO2$. Primes of the unit symbols, e.g., M', D', T', and Q' denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000. Commercially available MQ resins are, for example, trimethyl siloxy silicate with tradename BY11-018 available from Dow Corning.

The composition of the present invention may further contain a water-soluble polymer. It is believed that water-soluble polymers provide long-lasting effect. Useful water-soluble polymers include sodium carboxymethyl cellulose, polyvinyl pyrrolidone, polyvinyl alcohol, xanthan gum, agar, pulleran, bentonite, and mixtures thereof. Commercially available water-soluble polymers include the Carbopol series available from B. F. Goodrich Company, and PVP K-30 available from G.A.F. Chemicals.

Other components which can be formulated into the compositions of the present invention are; preservatives such as benzyl alcohol, methyl paraben, propyl paraben, imidazolidinyl area, and EDTA and its salts, perfumes, ultraviolet and infrared screening and absorbing agents such as ethylhexyl methoxycinnamate, and others.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLES 1–5

The following make-up compositions are formed by the following components using the method of preparation described herein:

| NO. | Component | Ex. 1 | Ex. 2 | Ex. 3 | Ex. 4 | Ex. 5 |
|---|---|---|---|---|---|---|
| 1 | Quaternium-18 Hectorite *1 | 0.2 | 0.2 | 0.2 | 0.2 | 0.3 |
| 2 | Cholesteryl Hydroxystearate *2 | 3 | 6 | | 5 | 5 |
| 3 | Cholesteryl Macadamiate *3 | | | 3 | | |
| 4 | Phenyl Trimethicone *4 | 5 | | | 5 | 7 |
| 5 | Liquid Petrolatum *5 | | 2 | 5 | | |
| 6 | Niacinamide *6 | 2 | | | 2 | 3.3 |
| 7 | Urea *7 | | 2 | | | |
| 8 | Glycerin *8 | 6 | 6 | 8 | 8 | 10 |
| 9 | Ozokerite *9 | 4 | 4 | 4 | 4 | 4 |
| 10 | Microcrystalline Wax *10 | 1.5 | 1.5 | 1.5 | 1.5 | 1.5 |
| 11 | Candelilla Wax *11 | 5 | 5 | 5 | 5 | 5 |
| 12 | Paraffin *12 | 3 | 3 | 3 | 3 | 2 |
| 13 | Diglyceryl Sebacate/Isopalmitate *13 | 22.3 | 22.3 | 22.3 | 22.3 | |
| 14 | Absorption Refined Lanolin *14 | 2.5 | 2.5 | 2.5 | 2.5 | 2.5 |
| 15 | Lanolin Oil *15 | 20 | 20 | 20 | | |
| 16 | Trioctanoin *16 | 7 | 7 | 7 | 16 | 20.2 |
| 17 | Isotridecyl Isononanoate *17 | 3 | 3 | 3 | 5 | 10 |
| 18 | Ethylhexyl methoxycinnamate | 3.5 | | | | |
| 19 | Preservatives | 0.5 | 0.5 | 0.5 | 0.5 | 0.5 |
| 20 | Powder Pigments | 15 | 15 | 15 | 20 | 30 |

Definitions of Components
*1 Quaternium-18 Hectrite: Bentone 38 available from Rheox. Inc.
*2 Cholesteryl Hydroxystearate: Salacos HS available from Nisshin Oil Mills, Ltd.
*3 Cholesteryl Macadamiate: Yofco MAC available from Nippon Fine Chemical
*4 Phenyl Trimethicone: Silicone Oil KF-56 available from Shinetsu Silicone
*5 Liquid Petrolatum: Liquid Petrolatum available from Witco Chemical
*6 Niacinamide: Niacinamide available from Roche
*7 Urea: Urea available from Taisei Chemical
*8 Glycerin: Glycerin USP available from Asahi Denka
*9 Ozokerite: Ozokerite wax SP-1021 available from Strahl & Pitsh
*10 Microcrystalline Wax: Multiwax 180-M Yellow available from Witco Chemical
*11 Candelilla wax: Candelilla wax NC-1630 available from Noda wax
*12 Paraffin: Paraffin wax FT-150 available from Sazole
*13 Diglyceryl Sebacate/Isopalmitale: Salacos DGS-16 available from Nisshin Oil Mills
*14 Absorption Refined Lanolin: Crodalan SWL available from Croda
*15 Lanolin Oil: Lanolin Oil available from Croda
*16 Trioctanoin: Hexalan available from Nisshin Oil Mills, Ltd.
*17 Isotridecyl Isononanoate: Crodamol TN available from Croda Method of Preparation The make-up compositions of Examples 1–5 are suitably prepared as follows: First, a mixture of component numbers 1 through 5 are heated to disperse at a speed of from 1500 rpm to 2500 rpm using a Homomixer at 90° C. in a sealed tank. Separately, a mixture of component numbers 6 through 8 are dissolved at 90° C. This solution (component numbers 6–8) is added to the dispersion (component numbers 1–5), and the mixture is further dispersed at a speed of from 5000 rpm to 7000 rpm using a Homomixer to form a hydrophobic gel. Next, component numbers 9 through 19, as present, are heated to dissolve at 80° C. in a sealed tank, followed by adding the above hydrophobic gel and component number 20, and the mixture is dispersed at 80° C. using a disper to make a lipophilic dispersion. The obtained dispersion is adjusted to a temperature of 80° C. Finally, the dispersion is filled in an air-tight container and allowed to cool to room temperature.

These embodiments represented by the previous examples have many advantages. For example, Examples 1 through 3 provide lipsticks which provide; improved lip suppleness, moisturization, and reduction of visible liplines and wrinkles to the lips. Example 4 provides a stick foundation. Example 5 provides a poured foundation. The foundations of Examples 4 and 5 provide; improved suppleness, moisturization, and reduction of visible lines and wrinkles to the skin, particularly facial skin. The make up compositions of Example 1 through 5 further have improved stability with regard to physical hardness, color, and sweat resistance.

It is understood that the examples and embodiments described herein are for illustrative purposes only and that various modifications or changes in light thereof will be suggested to one skilled in the art without departing from its spirit and scope.

What is claimed is:

1. A personal care composition comprising by weight:

(a) from about 5% to about 35% of a hydrophobic gel comprising:

i. a cholesteryl derivative;

ii. an oil swelling clay material;

iii. a non-volatile liquid oil; and iv. a polar solvent; and (b) a carrier which is substantially free of water, surfactant, and lecithin.

2. A personal care composition for use as a lipstick, a foundation, or a cream comprising by weight:

(a) from about 5% to about 35% of a hydrophobic gel comprising:

i. a cholesteryl derivative;

ii. an oil swelling clay material;

iii. a non-volatile liquid oil; and iv. a polar solvent; and (b) a carrier which is substantially free of water, surfactant, and lecithin, the carrier comprising one or more of solid wax, and a powder or coloring pigment.

3. The composition of claim 1 for use as a lipstick comprising weight:

(a) from about 10% to about 20% of a hydrophobic gel comprising, by weight of the entire composition:

i. from about 2% to about 7% of a cholesteryl derivative;

ii. from about 0.1% to about 1% of an oil swelling clay material;

iii. from about 2% so about 10% of a non-volatile liquid oil; and iv. from about 0.01% to about 10% of a polar solvent; and (b) a carrier which is substantially free of water, surfactant, and lecithin; the carrier comprising a solid wax and a powder or coloring pigment.

4. The lipstick composition of claim 3 further comprising a water-soluble humectant in an amount soluble in the polar solvent.

5. The lipstick composition of claim 4 wherein the water-soluble humectant is from about 1% to about 5% of niacinamide and the polar solvent is glycerin, the glycerin comprised at an amount of from about 0.01% to about 10%.

6. A method of making the composition of claim 1 comprising the steps of:
  (a) mixing the mixture of the cholesteryl derivative, the oil swelling clay material, and the non-volatile liquid oil at a speed of from about 1500 rpm to about 3000 rpm and at a temperature of from about 85° C. to about 95° C.;
  (b) mixing the polar solvent wish the mixture obtained in step (a) at a speed of at least about 4000 rpm and at a temperature of from about 85° C. to about 92° C.; and
  (c) mixing the carrier with the mixture obtained in step (b).

* * * * *